US009285354B2

(12) United States Patent
Carpenter et al.

(10) Patent No.: US 9,285,354 B2
(45) Date of Patent: Mar. 15, 2016

(54) SYSTEMS AND METHODS FOR THE DETECTION OF LOW-LEVEL HARMFUL SUBSTANCES IN A LARGE VOLUME OF FLUID (75) Inventors: Michael V. Carpenter, Idaho Falls, ID (US); Lyle G. Roybal, Idaho Falls, ID (US); Alan Lindquist, Cincinnati, OH (US); Vincente Gallardo, Cincinnati, OH (US)

(73) Assignee: The United States of America as represented by the Administrator of the U.S. Environmental Protection Agency, Washington, DC (US)

( * ) Notice: Subject to any disclaimer, the term of this patent is extended or adjusted under 35 U.S.C. 154(b) by 600 days.

(21) Appl. No.: 13/607,921

(22) Filed: Sep. 10, 2012

(65) Prior Publication Data
US 2013/0239666 A1 Sep. 19, 2013

Related U.S. Application Data (63) Continuation-in-part of application No. 11/695,432, filed on Apr. 2, 2007, now abandoned.

(51) Int. Cl.
*G01N 1/40* (2006.01)
*G01N 1/10* (2006.01)
(Continued)

(52) U.S. Cl.
CPC .......... *G01N 33/1866* (2013.01); *B01D 61/147* (2013.01); *B01D 63/02* (2013.01);
(Continued)

(58) Field of Classification Search
CPC ........ B01D 61/02; B01D 61/14; B01D 61/12; B01D 61/22; B01D 61/20; B01D 61/10; B01D 65/102; B01D 65/104; B01D 2311/08; B01D 2311/14; B01D 2311/25; B01D 2311/246; C02F 1/001; C02F 1/002; C02F 1/44; C02F 1/441; C02F 1/442; C02F 1/444; C02F 2103/007; C02F 2201/007; C02F 2209/005; C02F 2209/03; C02F 2209/42; G01N 1/02; G01N 1/10; G01N 1/14; G01N 1/40; G01N 1/4005; G01N 2001/4016; G01N 2001/4088

See application file for complete search history.

(56) References Cited

U.S. PATENT DOCUMENTS 4,879,040 A * 11/1989 Prince et al. .................. 210/637
5,193,709 A * 3/1993 Brassell ........................ 220/371

(Continued)

OTHER PUBLICATIONS

Lindquist et al. Using ultrafiltration to concentrate and detect *Bacillus anthracis, Bacillus atrophaeus* subspecies *globigii*, and Cryptosporidium parvum in 100-liter water samples. Journal of Microbiological Methods 70 (2007) 484-492.*

(Continued)

*Primary Examiner* — Katherine Zalasky
(74) *Attorney, Agent, or Firm* — Weiss & Moy, PC

(57) ABSTRACT

A method and device for the detection of low-level harmful substances in a large volume of fluid comprising using a concentrator system to produce a retentate and analyzing the retentate for the presence of at least one harmful substance. The concentrator system performs a method comprising pumping at least 10 liters of fluid from a sample source through a filter. While pumping, the concentrator system diverts retentate from the filter into a container. The concentrator system also recirculates at least part of the retentate in the container again through the filter. The concentrator system controls the speed of the pump with a control system thereby maintaining a fluid pressure less than 25 psi during the pumping of the fluid; monitors the quantity of retentate within the container with a control system, and maintains a reduced volume level of retentate and a target volume of retentate.

28 Claims, 6 Drawing Sheets

(51) Int. Cl.
  *B01D 61/14* (2006.01)
  *B01D 61/22* (2006.01)
  *G01N 33/18* (2006.01)
  *G01N 1/14* (2006.01)
  *B01D 63/02* (2006.01)
  *G01N 15/06* (2006.01)
  *B01D 61/10* (2006.01)
  *C02F 1/44* (2006.01)
  *G01N 15/00* (2006.01)

(52) U.S. Cl.
  CPC ............... *G01N 1/14* (2013.01); *G01N 1/4005* (2013.01); *G01N 15/0618* (2013.01); *G01N 2001/4088* (2013.01); *G01N 2015/0046* (2013.01); *G01N 2015/0065* (2013.01)

(56) References Cited

U.S. PATENT DOCUMENTS

| | | | | |
|---|---|---|---|---|
| 5,746,063 | A | * | 5/1998 | Hall et al. ........................ 62/331 |
| 6,001,244 | A | * | 12/1999 | Salter et al. .................... 210/104 |
| 2002/0043487 | A1 | * | 4/2002 | Schick ............................ 210/85 |
| 2003/0186428 | A1 | * | 10/2003 | Guillot et al. ............... 435/297.3 |
| 2006/0254981 | A1 | * | 11/2006 | Efraty ........................... 210/637 |

OTHER PUBLICATIONS

Hill et al. Development of a rapid method for simultaneous recovery of diverse microbes in drinking water by ultrafiltration with sodium polyphosphate and surfactants. Applied and Environmental Microbiology (Nov. 2005) 6878-6884.*

* cited by examiner

SYSTEMS AND METHODS FOR THE DETECTION OF LOW-LEVEL HARMFUL SUBSTANCES IN A LARGE VOLUME OF FLUID

RELATED APPLICATIONS

This U.S. non-provisional application is a continuation-in-part application of and claims priority to U.S. non-provisional application Ser. No. 11/695,432 filed Apr. 2, 2007, which is hereby fully incorporated by reference in its entirety.

GOVERNMENT RIGHTS

The United States Government has certain rights in this invention pursuant to Contract No. DE-AC07-05ID14517 between the United States Department of Energy and Battelle Energy Alliance, LLC.

FIELD OF THE INVENTION

Embodiments of the present invention relate to systems and methods for the detection of low-level harmful substances, preferably pathogens, in a fluid sample. Preferably, the systems and method described herein are used to detect low-level harmful substances in a large volume of fluid that would otherwise be undetectable without transporting the large volume of fluid to a testing site for concentration and analysis.

BACKGROUND OF THE INVENTION

There are many applications in which it is desired to detect the presence and, preferably the concentration of harmful substances even low-level, in a fluid. By way of example and not limitation, it may be desired to detect the presence and concentration of a microbial pathogen in a source of drinking water such as, for example, a lake, reservoir, river, stream, storage tank, water main, or well. Some harmful substances may be difficult to detect using conventional methods at lower concentrations. For instance, certain microbial pathogens may be harmful to human health at concentrations that are too low to accurately, reliably, and economically detect using conventional methods. Furthermore, in some situations, the sample size used in conventional detection methods may not provide testing results that reflect the actual concentration in the source from which the sample was obtained with an acceptable level of accuracy or certainty. For example, the concentration of a microbial pathogen in a few milliliters of water taken from a source of drinking water may not accurately represent the actual average concentration of the microbial pathogen in that source. As a result, analysis of multiple samples from a single fluid source may be required to determine the concentration of a harmful substance in the fluid source with an acceptable level of certainty.

For each of the above reasons, it has been proposed in the art to concentrate a fluid sample taken from a fluid source by a known concentration factor prior to determining the concentration of a harmful substance in the concentrated fluid sample. Once the concentration of the harmful substance in the concentrated fluid sample has been determined, the concentration in the unconcentrated fluid sample can be determined using the known concentration factor by which the fluid sample was concentrated.

As one example, it may be desired to know the concentration of a particular microbial pathogen in a source. A relatively large sample of water (e.g., about 100 liters) may be taken from the source. Some of the water may be separated or removed from the relatively large sample of water without separating or removing any significant number of the microbial pathogens of interest to provide a relatively smaller concentrated sample (e.g., about 1 liter) that includes substantially all of the microbial pathogens in the original relatively large sample of water. The identity and concentration of the microbial pathogens in the relatively smaller concentrated sample then may be determined, and the known identity and concentration of these pathogens in the concentrated sample may be used to determine the concentration in the original unconcentrated sample of water and, hence, the approximate concentration in the source.

Such methods may result in relatively higher concentrations of the harmful substance in the concentrated sample that are more readily detectible using conventional analytical techniques than if these analytical techniques were used to attempt to detect these harmful substances at the concentrations in the unconcentrated sample, and may result in measurements that more accurately reflect the actual presence and concentration of the harmful substance in the fluid source from which the sample was obtained for analysis.

There remains a need in the art for systems and methods that are portable, automated, that provide accurate and repeatable measurements, that provide acceptable concentration factors in acceptable amounts of time, and that minimize or reduce the risk of exposure of an operator to any harmful substance potentially carried by the fluid sample.

BRIEF SUMMARY OF THE INVENTION

A method and device for the detection of low-level harmful substances in a large volume of fluid comprising using a concentrator system to produce a retentate and analyzing the retentate for the presence of at one harmful substance. The concentrator system performs a method comprising pumping at least 10 liters of fluid from a sample source through a filter, where a percentage of the fluid crosses the filter wall and is discharged and the remaining percentage of water is recycled back to the filter inlet. The filter prevents the passage of at least one harmful substance. While pumping, the concentrator system diverts retentate from the filter into a container. While pumping, the concentrator system recirculates at least part of the retentate in the container again through the filter. The concentrator system also vents air to and from the container through an air filter, thereby preventing the release of at least one harmful substance out of the concentrator system. The concentrator system also controls the speed of the pump with a control system thereby maintaining a fluid pressure less than 25 psi during the pumping of the fluid; monitors the quantity of retentate within the container with a control system, and maintains a reduced volume level of retentate and a target volume of retentate. The concentrator system preferably maintains the volume of retentate in the container so that it is within an operator defined range and so that the final volume of retentate meets an operator specified value. The method of maintaining a reduced volume level of retentate and a target volume of retentate comprises detecting a value at least relating to the volume or weight of the retentate; and controlling the amount of retenate diverted in the step of diverting retentate.

Preferably, the concentrator system is monitored for leaks, preferably through the use of a water sensor. Preferably, the container containing the final volume of retentate is transported to a location different from the sample source, where it is subsequently analyzed for one or more harmful substances. Preferably, a blocking solution is added to the filter. A blocking solution is a solution for preventing one or more harmful substances from bonding with the filter, preferably polysorbate 80 and sodium polyphosphate. Polysorbate 80 is preferred as it makes the surface of the filter more hydrophilic. Sodium polyphosphate is preferred as it makes the surface of the filter electronegative. More preferably, the blocking solution further comprises one or more compounds designed to prevent foaming, preferably a silicone polymer-based antifoaming agent sold under the name ANTIFOAM A. In a preferred embodiment, the blocking solution consists essentially of water, polysorbate 80, ANTIFOAM A and sodium polyphosphate. Preferably, an elution solution is passed through the system after the large volume sample has been drawn into the system. The elution solution preferably comprises anything that will help loosen one or more harmful substances, more preferably polysorbate 80.

Preferably, the pumping is performed by a single pump. Preferably, the pumping pumps at least 100 liters, more preferably 100 liters. Preferably, the pumping is less than 2.9 liters per minute of fluid. Preferably the amount of retentate retained after being diverted produces less than 500 ml of retentate per 100 liters of fluid. Preferably the amount of retentate retained after being diverted produces less than 250 ml of retentate per 100 liters of fluid.

Preferably, the retentate is analyzed detecting the amount of one or more harmful substances. The concentration factor of the retentate is then preferably determined from the ratio of the pumped fluid to the electrically monitored quantity of retentate. Each detected one or more harmful substances in the transported retentate is then preferably multiplied by the determined concentration factor thereby producing the number of harmful substances in the pumped fluid.

Preferably, retentate is diverted from the filter into the container by directing the retentate along the inner walls of the container, which is preferred as it will minimize the generation of foam. Foam is preferably minimized as it will impeded analyzing of the resulting retentate and also poses as a threat to safety. In a preferred embodiment, a measuring device is connected to the container and the retentate is diverted perpendicular to the measuring device. This embodiment is advantageous as it will prevent the influx of retentate from affecting measurements, while also minimizing foam generation. Preferably, the fluid is pumped through at least one loop of conduit before it us pumped through the filter, thereby reducing vibrations which may damage the filter over time.

In some embodiments, the present invention includes methods of concentrating one or more harmful substances in a fluid. The methods include establishing circulation of fluid flow through a filter, causing fluid to exit the fluid circulation path through a filtering element of the filter, and preventing the one or more harmful substances from passing through the filtering element. The fluid circulation path may also pass through a retentate container and a pump, which may be used to drive fluid flow through the fluid circulation path. A control system may be used to control one or more components of the concentrator system. In some embodiments, the control system may be used to control a speed of the pump. In other embodiments, the control system may be used to control a quantity of retentate within the retentate container. In yet additional embodiments, the control system may be used to control both a speed of operation of the pump and a quantity of retentate within the retentate container.

In additional embodiments, the present invention includes systems for concentrating one or more harmful substances in a fluid. The systems include a circulating fluid pathway passing through a pump, a filter, and a retentate container. An effluent outlet line communicates with the circulating fluid pathway through a filtering element of the filter. A control system may be used to automatically control operation of one or more elements or components of the system (e.g., the pump) in response to a signal received from a sensor. For example, in some embodiments, the control system may include more than one sensor. For example, the control system may include one or more of a retentate sensor configured to sense a quantity of retentate within the retentate container, an effluent sensor configured to sense a quantity of effluent passing through the effluent outlet line, and a pressure sensor configured to sense a pressure at a location within the circulating fluid pathway. In some embodiments, the filter, retentate container, and the pump may be disposed within a housing or container for portability.

BRIEF DESCRIPTION OF THE SEVERAL VIEWS OF THE DRAWINGS

While the specification concludes with claims particularly pointing out and distinctly claiming that which is regarded as the present invention, the advantages of this invention may be more readily ascertained from the following description of the invention when read in conjunction with the accompanying drawings in which:

DETAILED DESCRIPTION OF THE INVENTION

Several of the illustrations presented herein are not meant to be actual views of any particular sample concentrator system or apparatus, but are merely idealized representations which are employed to describe the present invention. Additionally, elements common between figures may retain the same numerical designation.

A harmful substance is any substance harmful to any living organism, preferably humans, and without limitation whether such substance may be characterized as a pathogen, contaminant, a toxic substance, a substance artificially introduced into the fluid, or a naturally occurring substance. Preferably, the harmful substance is a pathogen. More preferably, the harmful substance is the causative agent for diseases such as tularemia, anthrax, smallpox, bubonic plague, viral hemorrhagic fevers, brucellosis, glanders, melioidosis, psittacosis, Q fever, salmonella, shigellosis, Typhus, staphylococcal infections, Viral encephalitis, cholera, cryptosporidiosis, *E. coli* O157:H7 infection, viral infections due to Nipah virus, Hantavirus, or H1N1, or a toxin such as Botulinum, Epsilon toxin of *Clostridium perfringens*, ricin, abrin, staphylococcal enterotoxin B, or a combination thereof. In preferred embodiments the harmful substances include the causative agents of tularemia, anthrax, smallpox, botulism, bubonic plague, viral hemorrhaigic fevers due to the contagiousness and high-mortality rate of these agents. In another preferred embodiment, the harmful substances include the causative agents of cholera and cryptosporidiosis due to the significant water supply threat of these agents.

A low-level harmful substance is a harmful substance not normally detectable without concentrating the harmful substance. More preferably, a low-level harmful substance is a substance having a level less than 1 microorganism per 1 liter.

Figure 1:
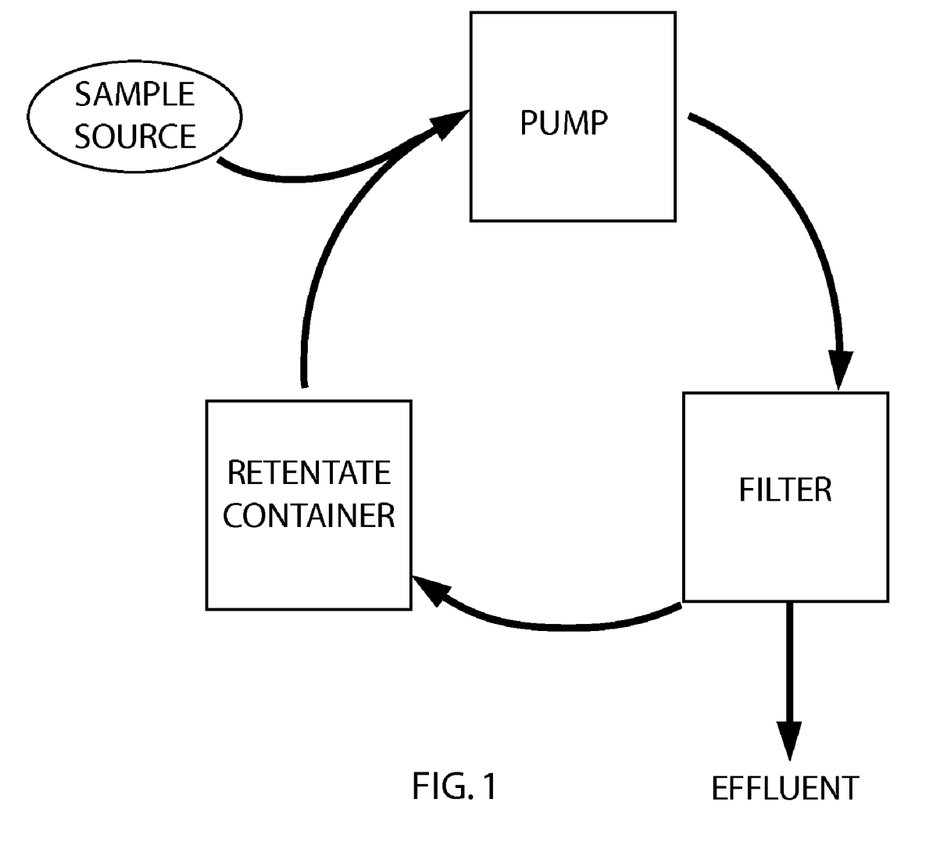
FIG. 1 is a simplified process flow diagram illustrating operational principles of embodiments of sample concentrator systems of the present invention.

FIG. 1 is a simplified process flow diagram illustrating principles that may be used to concentrate a harmful substance in a fluid sample according to embodiments of methods of the present invention. Such methods also may be carried out using embodiments of sample concentrator systems of the present invention. As shown in FIG. 1, a circular fluid path may be established using conduits such as pipes or hoses (not shown in FIG. 1) that passes through a pump, a filter, and a retentate container. As used herein, the terms "circular" and "circulating" mean and include a substantially continuous fluid path, without the exclusion of inlets thereto and outlets therefrom, and are not restricted to any particular physical path shape. The pump may be used to drive recirculating fluid flow within the circular fluid path. The fluid path may be primed with a fluid from a sample source that is potentially contaminated with a harmful substance, as also shown in FIG. 1. The sample source may comprise, for example, water from a lake, reservoir, river, stream, storage tank, water main or well. The filter may be configured to allow fluid to exit the circular fluid path as effluent, while preventing at least one harmful substance from exiting the circular fluid path. As fluid is removed from the circular fluid path through the filter, additional fluid may be drawn from the sample source as necessary to maintain a predetermined volume of fluid in the circular fluid path and within the retentate container. As the potentially contaminated fluid recirculates within the fluid circulation path, the concentration of one or more harmful substances may increase within the circular fluid path and the retentate container as additional pathogens and other harmful matter enters the circulating fluid path from the sample source but is prevented from leaving the circulating fluid path through the filter. After a predetermined or selected concentration factor has been achieved (i.e., a predetermined or selected volume of potentially contaminated fluid has been drawn into the fluid-circulation path and processed by the filter), a volume of the potentially contaminated concentrated fluid may be removed from the retentate container for testing and analysis. For example, the volume of the potentially contaminated fluid may be tested to detect the presence of one or more harmful substances, such as pathogens (e.g., microbial pathogens), for example, within the fluid taken from the sample source, and optionally, to estimate or determine the concentration of one or more harmful substances within the fluid taken from the sample source.

Figure 2:
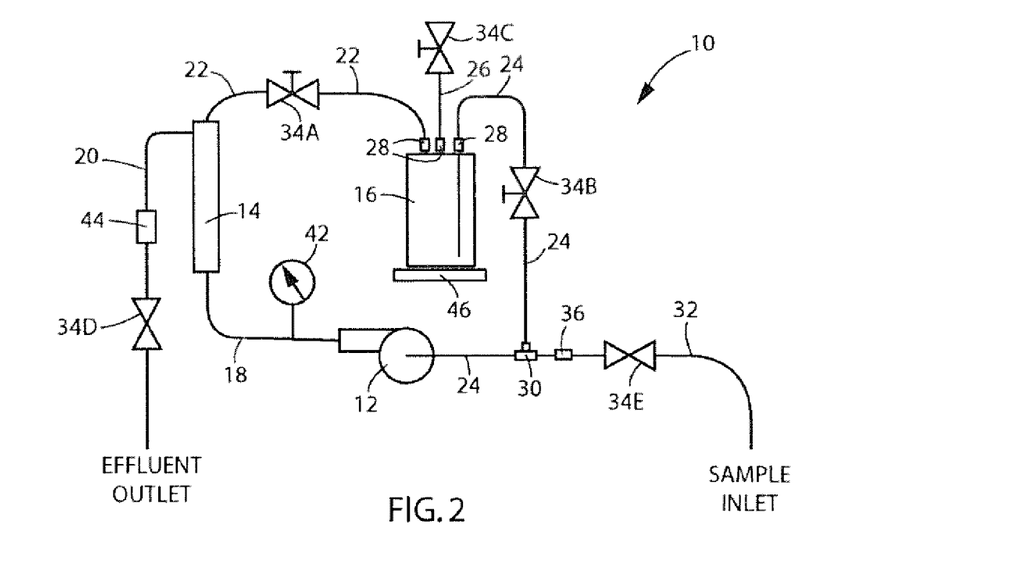
FIG. 2 is a process and instrumentation diagram schematically illustrating an embodiment of a sample concentrator system of the present invention.

FIG. 2 is a process and instrumentation diagram schematically illustrating an embodiment of a sample concentrator system 10 of the present invention. As shown in FIG. 2, the concentrator system 10 includes a pump 12, a filter 14, and a retentate container 16. As discussed in further detail below, the concentrator system 10 also includes a plurality of conduits defining a circulating fluid path passing through the pump 12, the filter 14, and the retentate container 16, as well as one or more conduits defining a sample source inlet line for drawing potentially contaminated fluid into the circulating fluid path, and one or more conduits defining an effluent outlet line for allowing fluid to exit the circulating fluid path.

The pump 12 is used to drive fluid flow of the potentially contaminated fluid through the concentrator system 10. In some embodiments, the pump 12 may comprise a peristaltic pump, in which one or more "rollers," "shoes," or "wipers" are caused to compress and wipe along the exterior surface of a flexible closed tube passing through the pump, which causes fluid to flow within the tube in the direction in which the wipers wipe along the tube. Using a peristaltic pump may prevent direct physical contact between the potentially contaminated fluid and any part of the pump, which may reduce the potential for contamination and corrosion, and prevents the accumulation of any harmful substance on parts or components of the pump, the presence of which harmful substance or substances could alter the detected concentration levels of the harmful substance within the circulating fluid path. Such peristaltic pumps are commercially available. As one particular non-limiting example, the pump 12 may comprise a MASTERFLEX® I/P® Precision Brushless Drive Model No. 77410-10, available from Cole-Parmer Instrument Co. of Vernon Hills, Ill., fitted with a MASTERFLEX® I/P® EASY-LOAD® Pump Head Model No. 77601-00, which is also available from Cole-Parmer Instrument Co. In additional embodiments, the concentrator system 10 may comprise any other type of pump capable of driving fluid flow through the concentrator system 10.

Figure 5:
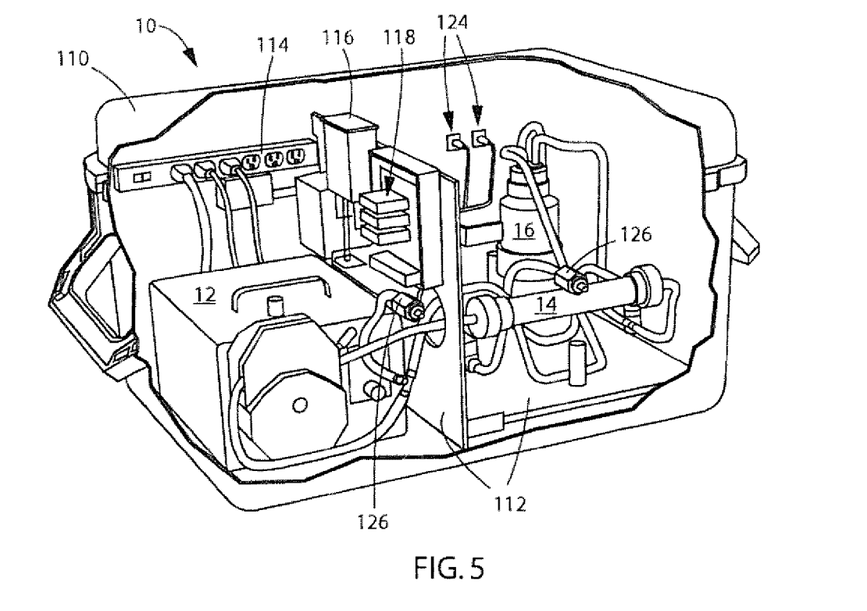
FIG. 5 is a partially cut-away perspective view illustrating one particular embodiment of a portable sample concentrator system of the present invention.

The pump 12 is preferably positioned to prevent any leak from the conduit from reaching any electronic components 118 the pump 12, or other electronics in the system. Although the pump 12 is shown in FIG. 5 facing the viewer for simplicity, the pump 12 is preferably positioned whereby the conduit is within in the same compartment (e.g. the right-hand side of FIG. 5). This embodiment is preferred to ensure that any leaks from the conduit are within a compartment designated for leaks and away from electronics that may be easily damaged.

With continued reference to FIG. 2, fluid may flow from the pump 12 to the filter 14 through a conduit 18. Although not shown for simplicity, the conduit 18 preferably has at least one loop to reduce vibrations which may damage the filter over time.

The filter 14 is used to allow fluid to exit the circulating fluid path of the concentrator system 10, while preventing one or more harmful substances, such as, for example, pathogens, from exiting the circulating fluid path of the concentrator system 10. In some embodiments, the filter 14 may comprise a plurality of longitudinally oriented hollow fibers disposed within a filter body, such as those filters disclosed in U.S. Pat. No. 5,531,848 to Brinda et al., the disclosure of which is incorporated herein in its entirety by this reference. By way of example and not limitation, each of the hollow fibers may have an average diameter of between about 100 microns and about 1,000 microns, and may be formed from a material having pores or apertures having an average pore size of between about fifty nanometers (50 nm) and about to microns (2μ). Such filters may have a molecular cutoff in the range from about 500 Da to about 500 kDa. More particularly in certain embodiments an ultrafiltration filter may have a molecular cutoff in the range from about 15 kDa to about 75 kDa. In other embodiments nanofilters with a molecular cutoff of less than about 500 Da may be used or microfilters with a molecular cutoff of greater than about 500 kDa may be used. The so-called filtrate or retentate moves longitudinally through the hollow fibers and through the filter body without passing through the pores in the walls of the fibers, while water and other low molecular weight components (often referred to as "permeate") pass through the pores in the walls of the fibers in a direction generally transverse to the general flow of the retentate through the fibers. In other words, the walls of the hollow fibers form or comprise the filtering element of the filter 14. Some fluid passes transversely through the walls of the hollow fibers, while other fluid and the harmful matter being concentrated passes longitudinally through the hollow fibers and the filter body, but not through the walls of the hollow fibers (the filtering element). As non-limiting examples, the filter 14 may comprise a HEMOCOR HPH® filter, Model No. HPH 1400 as sold by Minntech, APS series Dialyzer as sold by Asahi Kasei, EXELTRA PLUS 201 as sold by Baxter Corp, F200NR as sold by Fresenuis Miedical Co, and REXEED as sold by Asahi Kasei.

As shown in FIG. 2, an effluent outlet line 20, which communicates with the circulating fluid path through the filtering element of the filter 14, may extend from the filter 14 to a connector or fitting, to an effluent container, or to another suitable repository for the effluent. In situations in which the sample source is relatively large, such as, for example, drinking water storage tank, a drinking water distribution system, a lake, reservoir, river, a stream, a water main or stream, the effluent outlet line 20 may extend back to the sample source at a location sufficiently remote from the location at which potentially contaminated fluid is being drawn into the concentrator system 10 so as to not affect the concentration of harmful substances in the fluid being drawn into the concentrator system 10.

One or more conduits 22 may be used to allow retentate (fluid and harmful matter that has not passed through the filtering element of the filter 14) to flow from the filter 14 to the retentate container 16.

The retentate container 16 is used to accumulate a desired volume of potentially contaminated fluid or retentate in the concentrator system 10 for subsequent testing and analysis. In some embodiments, the retentate container may be easily removable from the concentrator system 10 to allow an operator to remove the retentate container 16 from the concentrator system 10 to facilitate transportation or shipment of the retentate container 16 and the potentially contaminated retentate therein to a laboratory or other location for testing and analysis. Furthermore, the retentate container 16 may be configured to minimize exposure of an operator of the concentrator system 10 to any pathogens or other harmful substances that may be present within the retentate container 16 when the operator removes the retentate container 16 from the concentrator system 10 or otherwise handles the retentate container 16.

By way of example and not limitation, the retentate container 16 may comprise a glass or plastic carboy or bottle. In some embodiments, the retentate container 16 may comprise a material that is autoclavable such as, for example, glass or polypropylene. As one particular nonlimiting example, the retentate container 16 may comprise a NALGENE® autoclavable polypropylene one liter (1 L) bottle. Such bottles are commercially available from, for example, Thermo Fisher Scientific Inc. of Waltham, Mass.

With continued reference to FIG. 2, one or more conduits 24 may be used to allow retentate to flow from the retentate container 16 back to the pump 12. As shown in FIG. 2, in some embodiments, one end of a conduit 24 may be positioned in the lower interior region of the container 16 to allow fluid within the retentate container 16 to be drawn into the conduit 24 by the pump 12 even when the fluid level within the retentate container is low. A vent line 26 may also be used to provide communication between the upper interior region of the container 16 and the exterior of the container 16 to allow venting of the retentate container 16 as necessary or desired. In some embodiments, the container 16 may be fitted with a so-called "filling/venting cap," which may be used to couple the conduit 22, the conduit 24, and the vent line 26 to the retentate container 16. Such filling/venting closures also are commercially available from, for example, Thermo Fisher Scientific Inc. of Waltham, Mass.

As shown in FIG. 2, in some embodiments, a coupler 28 may be provided in one or more of the conduits 22, 24, and 26 at a location proximate the retentate container 16 to allow the retentate container 16 to be quickly and easily disconnected from the concentrator system 10. By way of example and not limitation, each coupler 28 may comprise a so-called male-to-female Luer Lock type connector or other suitable connectors such as for example, straight connectors, hose connectors, barb connectors, ISO connectors, sanitary connectors, or quick disconnect connectors. Optionally, one or more of the couplers 28 may comprise a stopcock.

As shown in FIG. 2, a three-way connector 30 may be used to couple a sample inlet line 32 to the conduits 24 extending between the retentate container 16 and the pump 12. The sample inlet line 32 may be used to draw potentially contaminated fluid into the concentrator system 10 by the pump 12 from a sample source.

The fluid concentrator system 10 may comprise one or more valves that can be used to selectively control fluid flow through the system 10. For example, a valve 34A may be provided along the conduit 22 extending between the filter 14 and the retentate container 16, a valve 34B may be provided along the conduit 24 extending between the retentate container 16 and the pump 12, and a valve 34C may be provided along the vent line 26. The fluid concentrator system 10 also may comprise a valve 34D along the effluent outlet line 20 and a valve 34E along the sample inlet line 32, as also shown in FIG. 2. A check valve 36 also may be provided along the sample inlet line 32 that allow fluid flow in only one direction therethrough (i.e., in the direction extending from the fluid sample source to the pump 12) to prevent back flow of fluid out from the fluid circulation path of the concentration system 10 through the sample inlet line 32.

The valves 34A-34E may comprise on-off shutoff type valves, or they may comprise variable flow control valves. By way of example and not limitation, the valves 34A-34E may comprise pinch valves that are configured to pinch flexible tubing of the conduit extending there through. In some embodiments, such pinch valves may be configured to pinch the flexible tubing of the conduit using an electrically operated solenoid or a pneumatically or hydraulically operated drive element, and may be automatically actuated by a signal received from a controller, as discussed in further detail below. In other embodiments, one or more of the valves 34A-34E may be manually operated and may comprise, for example, a simple manually actuated tubing clamp.

In some embodiments, each of the conduits 18, 22, 24, as well as the effluent outlet line 20, the vent line 26, and the sample inlet line 32 may comprise hollow flexible polymeric tubing.

In some embodiments, one or more features or functions of the sample concentrator system 10 may be substantially automatically operated or controlled using a controller, and the concentrator system 10 may include one or more sensors, meters, or gauges for monitoring one or more conditions of the concentrator system 10 and relaying signals indicative of such conditions to the controller to enable the controller to automatically adjust one or more operating parameters of the system 10 in response to the signals as necessary or desired.

By way of example and not limitation, the sample concentrator system 10 may include one or more pressure gauges for measuring the fluid pressure at selected locations within the system 10. As shown in FIG. 2, the concentrator system 10 may include a pressure gauge 42 for measuring the pressure of the fluid within the conduit 18 extending between the pump 12 and the filter 14. The pressure gauge 42 may be configured to generate a signal indicative of the pressure and to relay the signal to a controller, described in further detail below. The sample concentrator system 10 also may include one or more flow sensors for measuring the rate of fluid flow at selected locations within the system 10.

As shown in FIG. 2, the concentrator system 10 may include a flow sensor 44 for measuring the flow rate of fluid exiting the concentrator system 10 through the effluent outlet line 20. The flow sensor 44 may be configured to generate a signal indicative of the flow rate and to relay the signal to the controller.

The sample concentrator system 10 also may include one or more sensors for measuring the volume of retentate within the retentate container 16. Such sensors may be configured to measure the volume of the retentate within the retentate container 16 without requiring direct physical contact between any part of the sensor and the retentate within the container 16. By way of example and not limitation, the concentrator system 10 may include a load cell 46 for measuring the weight of the volume of retentate within the retentate container 16, as shown in FIG. 2. The weight of the volume of retentate may be used to calculate the volume of the retentate using a known approximate value of the density of the retentate. In additional embodiments, an optical sensor, a proximity sensor, or any other type of sensor may be used to measure the volume of the retentate within the retentate container 16.

Figure 3:
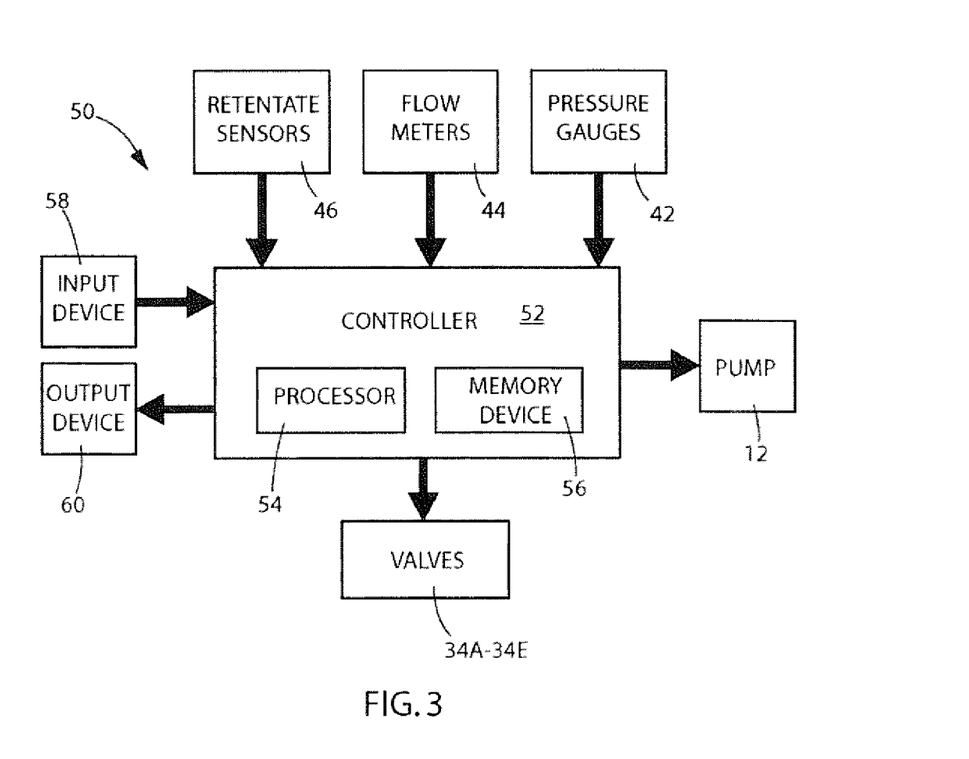
FIG. 3 is a Nock diagram schematically illustrating an embodiment of a control system that may be used to control operation of the sample concentrator system shown in FIG. 2.

FIG. 3 is a Nock diagram schematically illustrating an embodiment of a control system 50 that may be used to control operation of the sample concentrator system 10 shown in FIG. 2. The control system 50 may comprise a controller 52. The controller 52 may comprise, for example, a microcontroller, ASIC (Application Specific Integrated Controller), computer (e.g., a portable computer, a desktop computer, a personal data assistant (PDA), etc.) or a programmable logic controller. The controller 52 may comprise at least one electronic signal processor 54 (i.e., a microprocessor) and at least one memory device 56 (i.e., a random access memory (RAM) device, a read only memory (ROM) device, a Flash memory device, etc.) for storing data therein in electrical communication with the electronic signal processor 54.

As shown in FIG. 3, the controller 52 may be configured to receive a signal from each of the pressure gauge 42, the flow sensor 44, and the load cell 46 previously described in relation to FIG. 2, as well as any additional gauges, sensors, or meters of the concentrator system 10. The controller 52 also may be configured to control operation of the pump 12. For example, the controller 52 may be configured to relay one or more signals to the pump 12 to cause the pump 12 to start the pump, to stop the pump, to adjust the speed of operation of the pump, and to change the direction in which the pup head rotates. The controller 52 also may be configured to selectively actuate or otherwise control one or more of the valves 34A-34E, as previously discussed with reference to FIG. 2.

With continued reference to FIG. 3, the control system 50 may further comprise at least one input device 58 for enabling an operator to input one or more commands to the control system 50 of the fluid concentrator system 10, and at least one output device 60 for outputting information to the operator. By way of example and not limitation, the input device 58 may comprise at least one of a button, a switch, a keypad, a touchpad or touchscreen, a keyboard, and a mouse or other pointing device, and the at least one output device 60 may comprise at least one of a device for emitting an visible or audible signal, a display screen or monitor, and a printer.

In this configuration, the control system 50 may be configured under control of a computer program to substantially automatically control the various elements, components, and subsystems of the sample concentrator system 10 when concentrating a fluid sample. By way of example and not limitation, the control system 50 may be configured under control of a computer program (which optionally may be recorded in memory of the at least one memory device 56 of the controller 52) to perform the sequence of operations illustrated in the flow chart shown in FIGS. 4A-4C.

Figure 4A:
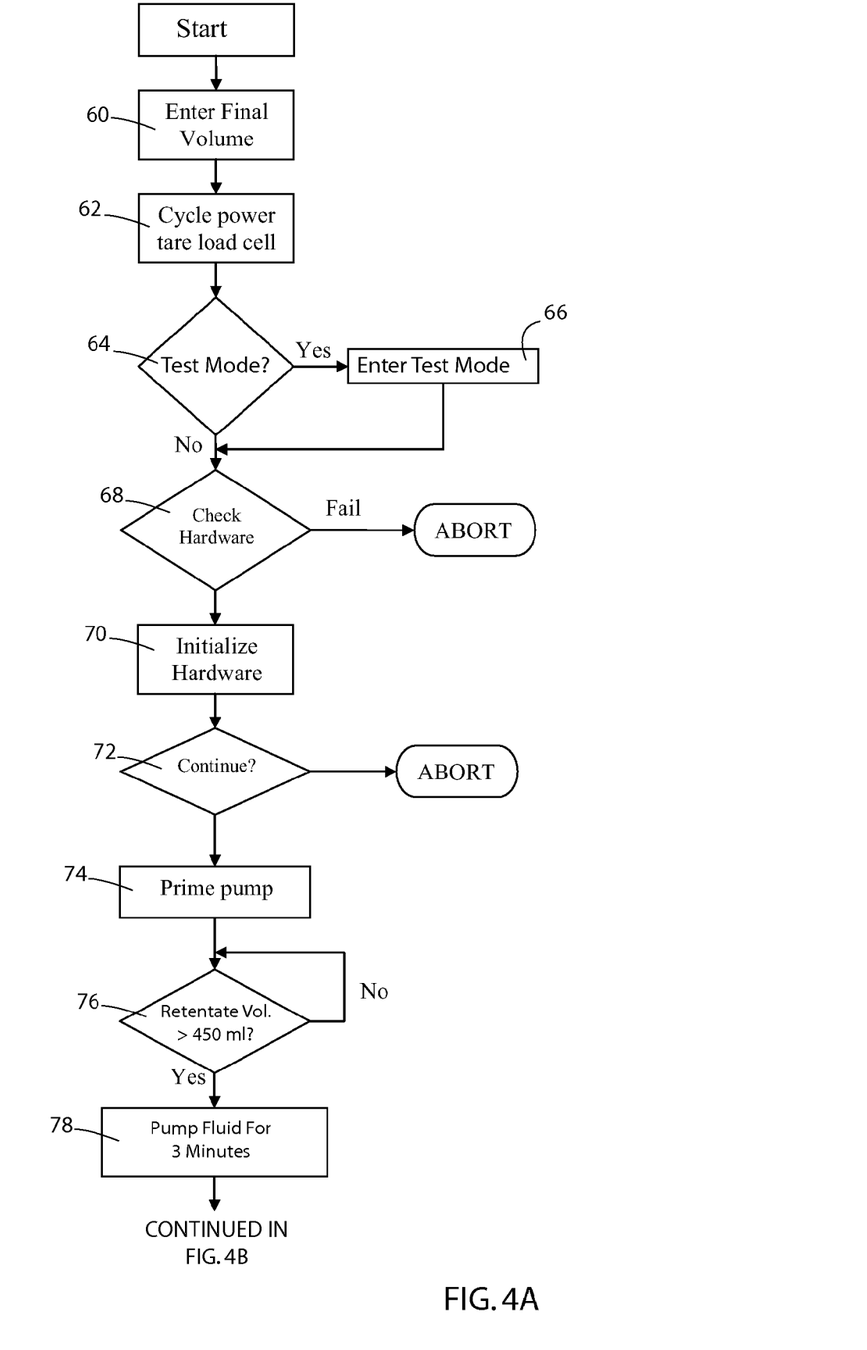
FIGS. 4A-4C illustrate a flow chart showing a sequence of operations that may be performed by the control system shown in FIG. 3.

Referring to FIG. 4A, upon receipt of an input signal received from an operator through the input device 58, the control system may be configured to request that the operator input the total volume of effluent to be discharged from the effluent outlet line 20 (FIG. 2) during a concentration process as shown at activity 60, which, in effect, may determine the concentration factor to be achieved during the concentration process. After the volume has been input to the control system 50 by the operator, the control system 50 may cycle power to the various components of the concentrator system 10 that require power and tare the load cell 46 or any other sensor, gauge, or meter that requires taring, as shown at activity 62. The control system 50 may be configured to ask the operator if it is desired to enter a test mode (e.g., for calibration), as shown at decision point 64. If yes, the control system 50 may enter the test mode as shown at activity 66, the details of which may be customized to particular applications and are not described in detail herein. If the decision at decision point 64 is no, the control system 50 may be configured to check hardware (e.g., one or more of the pump 12, the pressure gauge 42, the flow sensor 44, and the load cell 46) for errors, as shown at decision point 68. If one or more of the hardware components fails the hardware check, the process may abort and an error message may be conveyed to the operator via the output device 60 (FIG. 3). If all hardware passes the hardware check, the control system 50 may initialize the hardware as shown at activity 70 and may enter a ready mode at which it waits for an input signal from the operator to initialize a concentration process or cycle, as illustrated at decision point 72.

If the control system 50 receives an input signal from the operator to initialize a concentration process or cycle, the control system 50 may prime the pump 12 (FIG. 2), as indicated at activity 74. For example, priming the pump 12 may include operating the pump 12 at a predetermined speed for a predetermined amount of time, and then determining whether the volume of retentate within the retentate container 16 (FIG. 2) is greater than a predetermined minimum value (e.g., four hundred and fifty milliliters (450 ml)), as shown at decision point 76. If the retentate volume is below the minimum value, the control system 50 may be configured to repeat the pump priming activities, as shown in FIG. 4A. If the retentate volume is above the minimum value, the control system 50 may be configured to cause the pump 12 to operate at a predetermined speed for a predetermined amount of time (e.g., three minutes) to cause fluid to flow through the fluid circulation path (i.e., from the pump 12, through the filter 14, the retentate container 16, and back to the pump 12), as shown at activity 78 in FIG. 4A.

Figure 4B:
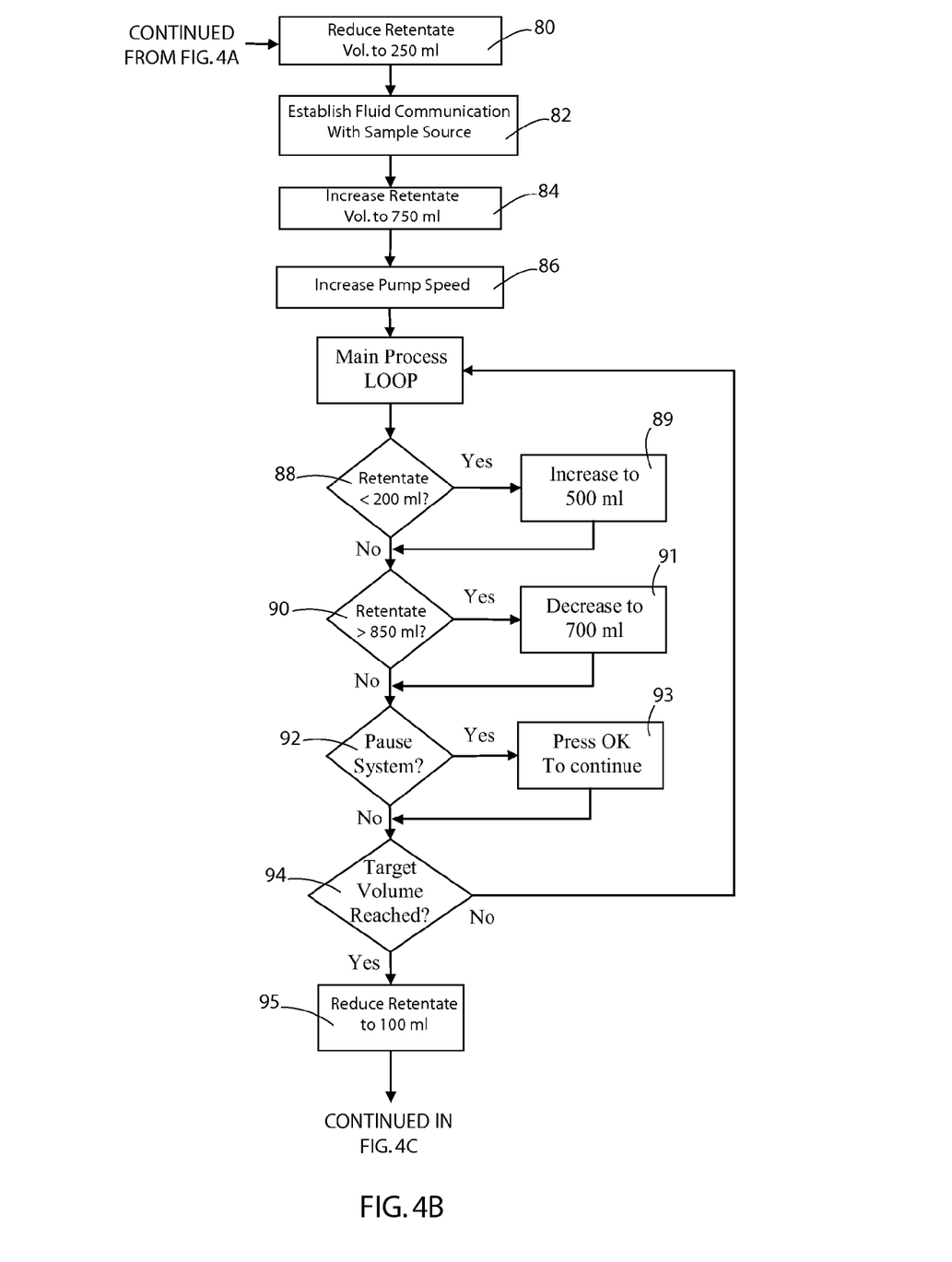

Referring to FIG. 4B, after the pump 12 has pumped fluid through the fluid circulation path, the control system 50 may be configured to reduce the volume of retentate in the retentate container 16 to a reduced level (e.g., about two hundred and fifty milliliters (250 ml), as shown at activity 80, by closing the valve 34E (FIG. 12) and operating the pump 12 until the reduced volume level is achieved. After the reduced volume level of retentate has been achieved, the control system 50 may be configured to stop the pump 12 and to provide fluid communication to the sample source, as shown at activity 82, by opening the valve 34E. The control system 50 may be configured to then close the valve 34B and operate the pump 12 to draw potentially contaminated fluid into the fluid circulation path of the concentrator system 10 until an increased desired target volume of retentate has been obtained in the retentate container 16 (e.g., about seven hundred and fifty milliliters (750 ml)), as shown at activity 84. After the desired target volume of retentate has been obtained in the retentate container 16, the control system 50 may be configured to increase the operating speed of the pump 12 to a desired operating speed (which may be a maximum operating speed of the pump 12), as shown at activity 86, and to then enter a main process loop.

The control system 50 then may be configured to enter a main process loop in which the pump 12 is operated to pump fluid through the fluid circulation path and to selectively draw additional potentially contaminated fluid into the fluid circulation path through the sample inlet line 32 as required to maintain the volume of retentate within the retentate container 16 within selected predetermined limits as fluid exits the fluid circulation path through the effluent outlet line 20. This overall process may concentrate one or more harmful substances within the retentate.

For example, as shown in FIG. 4B, the control system 50 may be configured to determine whether the retentate volume in the retentate container 16 is below a lower threshold level (e.g., two hundred milliliters (200 ml)) using the load cell 46, as shown at decision point 88. If the volume is below the threshold level, the volume may be increased to a level within the selected predetermined limits (e.g., five hundred milliliters (500 ml)), as shown at activity 89. If the volume is above the lower threshold level, the control system 50 may be configured to determine whether the retentate volume in the retentate container 16 is below an upper threshold level (e.g., eight hundred and fifty milliliters (850 ml)) using the load cell 46, as shown at decision point 90. If the volume is above the upper threshold level, the volume may be decreased to a level within the selected predetermined limits (e.g., seven hundred milliliters (700 ml)), as shown at activity 91.

With combined reference to FIG. 4B and FIG. 2, in the processes described above, the volume of retentate in the retentate container 16 may be increased by, for example, closing valve 34B, opening the valve 34E, and operating the pump 12 to draw additional sample fluid into the circulating fluid path. The volume of retentate in the retentate container 16 may be decreased by, for example, opening the valve 34B, closing the valve 34E, and operating the pump 12 to force additional effluent out from the circulating fluid path through the effluent outlet line 20. The valve 34A also may be dosed as necessary or desired when decreasing the volume of the retentate within the retentate container 16.

As the pump 12 circulates fluid through the filter 14, a pressure differential may be generated across the filter 14. In other words, the fluid pressure in the conduit 18 may be relatively higher than the fluid pressure in the conduit 22. The volume of effluent discharged through the effluent outlet line 20 may be at least partially a function of this pressure differential, and the pressure differential may be at least partially a function of the operating speed of the pump 12. If the valve 34C on the vent line 26 (FIG. 2) is maintained in the closed position, a back pressure may be generated within the conduit 22 upon operation of the pump 12. Providing a back pressure within the conduit 22 (and within the retentate container 16) of about thirteen thousand eight hundred Pascals (13,800 Pa) (about two pounds per square inch (2 PSI)) or more may help to stabilize the fluid level of the retentate in the retentate container 16 and may help to force effluent out the effluent outlet line 20 through the filter 14. This back pressure may be a function of the pressure within the conduit 18, the flow characteristics of the filter 14, and the state of the various valves 34A-34E. As a result, it can be determined (e.g., using empirical studies) what the pressure in the conduit 22 will be for a given pressure within the conduit 18 and state of the valves 34A-34E. In other words, the pressure differential between the conduit 18 and the conduit 22 can be deduced using the known pressure within either the conduit 18 or the conduit 22, and the state of the valves 34A-34E for any particular embodiment of a concentrator system 10.

In some embodiments, it may be desirable to maintain the pressure differential between the conduit 18 and the conduit 22 within a predetermined range of pressures. For example valve 34A may be an adjustable valve used to create a pressure differential. By way of example and not limitation, it may be desirable to maintain this pressure differential between about thirty five thousand Pascals (35,000 Pa) (about five pounds per square inch (5 PSI)) and about one hundred and seventy two thousand Pascals (172,000 Pa) (about twenty five pounds per square inch (25 PSI)). Therefore, in some embodiments, the control system 50 may be configured to monitor the pressure within the conduit 18 using the pressure gauge 42, and to automatically adjust the operating speed of the pump 12 so as to maintain this pressure differential within the predetermined range of pressures.

With continued reference to FIG. 4B, in some embodiments, the control system 50 may be configured to allow an operator to pause operation of the concentrator system 10 (e.g., the pump 12) at any time during the main process loop by, for example, providing an input signal using the input device 58 (FIG. 3). Therefore, in some embodiments, if the volume of retentate within the retentate container 16 is below the upper threshold level, the control system 50 may be configured to determine whether an input signal has been received indicating that the operator wishes to pause operation of the concentrator system 10, as shown at decision point 92. If such a signal has been received, the control system 50 may be configured to pause or wait until the operator provides an additional input signal indicating that it is desired to resume operation, as shown at activity 93. If no such signal has been received, the control system 50 may be configured to determine whether the total volume of effluent that has been discharged from the effluent outlet line 20 is greater than or equal to that entered by the operator during activity 60 (FIG. 4A) as the desired target volume, as shown at decision point 94. If the desired final volume has not been achieved, the control system 50 may be configured to repeat the main process loop, as shown in FIG. 4B. If the desired target volume has been achieved, the control system 50 may be configured to close the valve 34E to prevent additional sample fluid from being drawn into the concentrator system 10, and to optionally reduce the volume of retentate within the retentate container 16 to a desired target sample volume (e.g., about one hundred milliliters (100 ml)), as shown at activity 95.

Figure 4C:
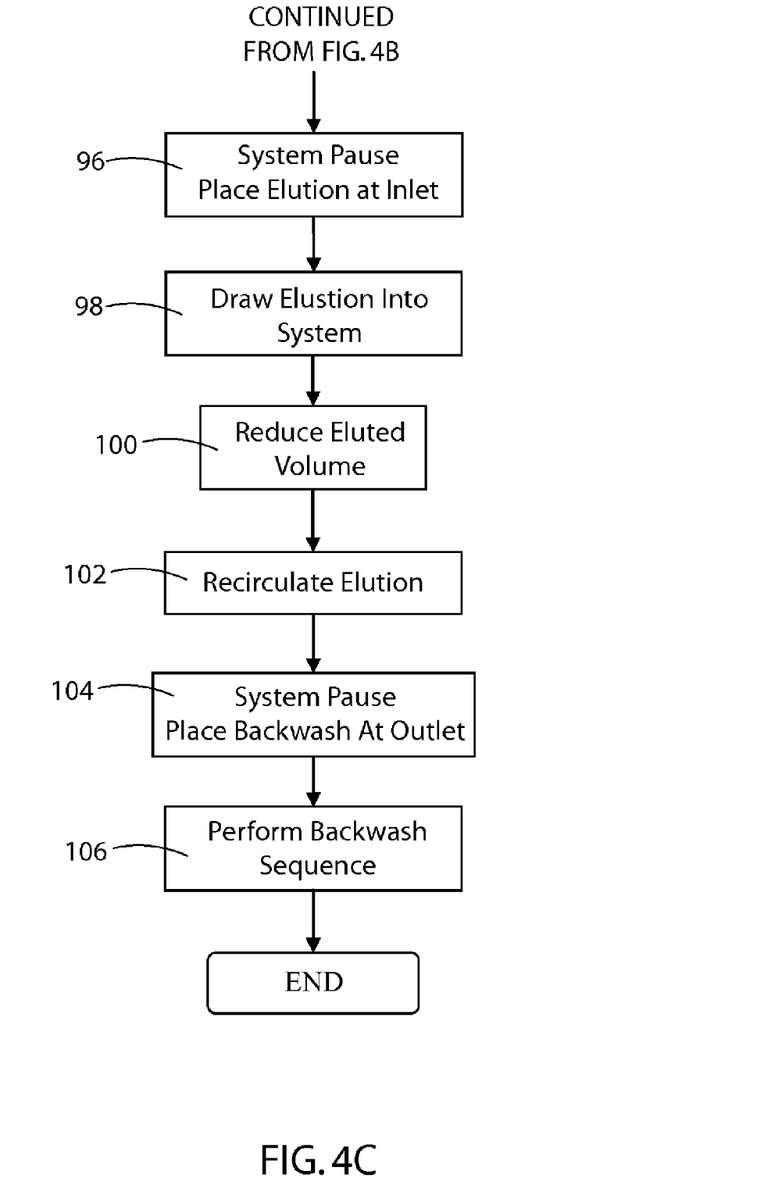

Referring to FIG. 4C, the control system 50 may be configured to then pause operation of the concentrator system 10 (e.g., the pump 12) to allow the operator to remove the final sample volume from the concentrator system 10 for testing and analysis, as shown at activity 96. In some methods, the entire retentate container 16 may be removed from the concentrator system for transportation or shipment to a remote location for testing and analysis. The pause operation is preferably used to allow the operator to change the supply side source such as a carboy. For example, a 50 liter carboy weighs approximately 50 kg, using multiple supply side containers may be advantageous when the source is not a large body such as a kitchen or bath sink, lake, pond, or stream.

Optionally, after the final sample volume from the concentrator system 10, the control system 50 may be configured to enable an operator to perform one or more rinsing or washing operations. For example, it may be desired to flush the system 10 with an eluent. As shown at activity 96, fluid communication may be established between the sample inlet line 32 and an eluent. The control system 50 may be configured to then operate the pump 12 at a predetermined speed for a predetermined amount of time to draw the eluent into the concentrator system 10 through the sample inlet line 32, as shown at activity 98.

As shown at activity 100, the volume of eluent being discharged from the concentrator system 10 through the effluent outlet line 20 may be reduced by closing the valve 34D, after which the control system 50 may be configured to operate the pump 12 at a predetermined speed for a predetermined amount of time to recirculate the eluent through the fluid circulation path, as shown at activity 102.

The control system 50 may be configured to then pause operation of the concentrator system 10 to enable an operator to configure the system 10 for an optional backwash process by establishing fluid communication between the effluent outlet line 20 and a backwash eluent, as shown at activity 104. The control system 50 may be configured to perform a backwash sequence, as shown at activity 106. By way of example and not limitation, the backwash sequence may comprise, for example, closing the valves 34A and 34E and operating the pump 12 at a predetermined speed 12 for a predetermined amount of time to draw the backwash eluent into the concentrator system 10 through the effluent outlet line 20 and the filter 14. Backwashing the filter 14 in this manner may help to dislodge and otherwise free matter that has accumulated in the hollow fibers of the filter 14, and to allow such matter to be discharged from the concentrator system 10 through the sample inlet line 32 or through the retentate container 16.

Optionally, embodiments of concentrator systems 10 of the present invention may be configured as a portable system that can be transported or shipped to a location of a potentially contaminated fluid sample source, such as, for example, a lake, reservoir, river, stream, or well.

FIG. 5 is a partially cut-away side perspective view of one particular portable embodiment of the concentrator system 10 that is represented schematically in FIG. 2. As shown in FIG. 5, the portable concentrator system 10 includes a portable outer housing 110, which may comprise one or more handles and one or more wheels to facilitate transportation of the concentrator system 10. As shown in FIG. 2, the pump 12, the filter 14, and the retatentate container 16 each may be secured within the housing 110. For example, one or more of the pump 12, the filter 14, and the retatentate container 16 may be structurally fastened or otherwise secured to an internal frame member 112 positioned within the container, and the internal frame member 112 optionally may be fastened or otherwise secured to the interior of the housing 110. Each of the other various elements and components of the concentrator system 10 shown in FIG. 2 also may be secured within the housing 110.

The portable concentrator system 10 shown in FIG. 5 may include a power distributor 114, which may be used to distribute power to the various components of the concentrator system 10 requiring independent power for operation (e.g., the pump 12). The portable concentrator system 10 may operate on power supplied by at least one of an external power supply grid and an internal power source (e.g., a battery, fuel cell, generator, etc.) For example, the portable concentrator system 10 may comprise an internal battery 116 that may be used to power the various components of the concentrator system 10.

As shown in FIG. 5, the portable concentrator system 10 also may include various electronic components 118, which optionally may be mounted to the internal frame member 112. The electronic components 118 may comprise, for example, the controller 52 of the control system 50 (FIG. 3), an electronic meter for the load cell 46 (FIG. 2), electronic components associated with flow meters or pressure gauges, relay boxes, fuse boxes, etc.

In some embodiments, the portable concentrator system 10 may comprise one or more data ports 124 for transmitting electrical signals between the electronic components within the housing 110 and electronic devices outside the housing 110. By way of example and not limitation, the controller 52 of the control system 50 shown in FIG. 3 may comprise a portable computer device located outside the housing 110, and electrical communication may be established between the portable computer device and the other components of the control system 50 shown in FIG. 3 (which may be disposed within the housing 110) through one or more data ports 124. Such data ports 124 may be mounted through the wall of the container, as shown in FIG. 5, to enable electrical communication between the electronic components within the housing 110 and electronic devices outside the housing 110 without requiring that a lid or cover of the housing 110 be removed or opened.

Preferably, the housing 110 comprises one or more, more preferably a plurality of, provisions for preventing the release of the retentate in the retentate container 16, particularly aerosolized retentate. In one embodiment, the housing 110 comprises one or more windows (not shown for simplicity) to enable an operator to visually inspect the various components of the concentrator system 10 within the housing 110 without requiring that a lid or cover of the housing 110 be removed or opened. Preferably additional interior enclosures within the device are also used to limit the area of exposure upon the release of the retentate. Preferably, the housing 110 further comprises one or more leak detection sensors, thereby allowing for the detection, and preferably notification to the operator, of a breach in the system. Preferably, all electronics are contained in separate, isolated electronics compartment 113. Preferably, the isolated electronics compartment 113 is sealed to prevent any liquids from entering the compartment, while also reducing thermal conductivity that would otherwise heat the retentate. This is preferred as many pathogens are sensitive to changes in temperature, and the heat generated by the electrical components may have an adverse impact on the results of the viability assays. Preferably, the electronics compartment 113 is designed to be removed for decontamination without rexposing the sensitive electronics to potentially harsh chemical disinfectants. Thus, even if the enclosed fluid path were breached, resulting in contamination of that portion of the device, a substantial portion of the device could be readily decontaminated and rapidly restored to operations. The entire device is preferably enclosed in an outer enclosure. The outer enclosure is preferably designed to prevent penetration of environmental elements (dust and rain) from the outside, as well as containing any potential spills, leaks or aerosols within the device.

Preferably, the filter 14, pressure transducer 42 as shown in FIG. 2, and the various conduit are all designed for user removal to prevent cross contamination. Preferably, they are designed for user removal by the use of one or more quick disconnect fittings that act as shut-off valves when disconnected. Preferred embodiments, as described above, have been able to detect with 99% confidence 6 bacterial endospores in 100 liters of water. Therefore, with this level of sensitivity, it is essential the various components be replaced before each run to ensure that cross contamination is prevented.

Figure 6:
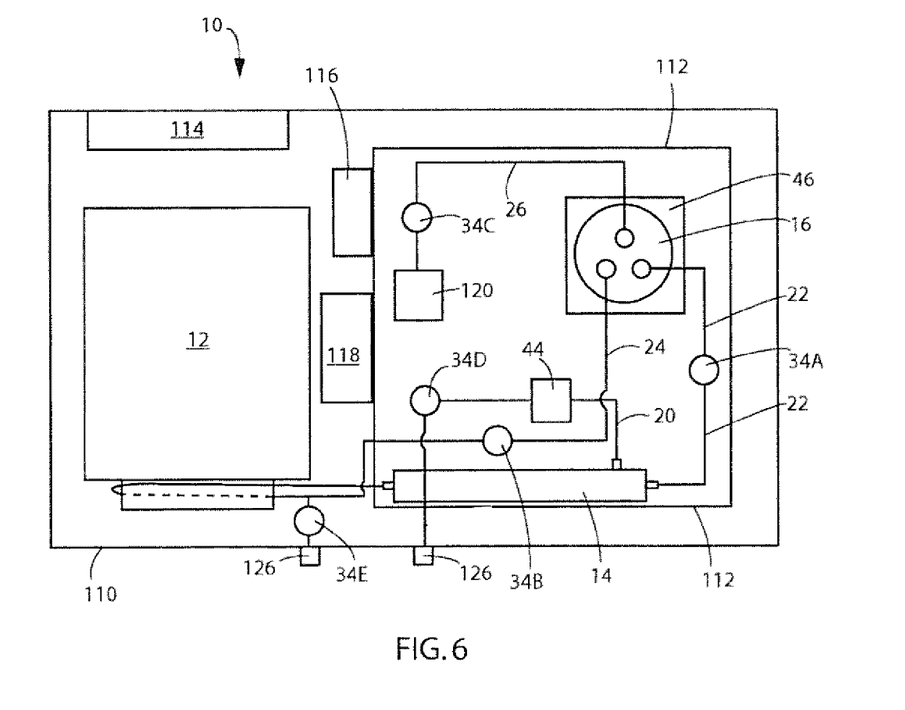
FIG. 6 is a schematic top plan view of the portable sample concentrator system shown in FIG. 5 and illustrates one example of a manner in which the various elements, components, and subsystems of the portable sample concentrator system may be located and secured within an outer housing of the portable sample concentrator system.

FIG. 6 is a schematic top plan view of the portable concentrator system 10 shown in FIG. 5 and illustrates the physical layout of the various operational elements, components, and subsystems of the portable concentrator system 10 within the housing 110. Many other physical layouts are contemplated and embodiments of concentrator systems of the present invention may have physical layouts other than that shown in FIGS. 5 and 6.

As shown in FIGS. 5 and 6, a coupler 126 also may be mounted through the housing 110 for coupling an external conduit (not shown) to the sample inlet line 32 (FIG. 2), and an additional coupler 126 also may be mounted through the housing 110 for coupling another external conduit (not shown) to the effluent outlet line 20 (FIG. 2). By way of example and not limitation, the couplers 126 may comprise, for example, straight connectors, hose connectors, barb connectors, ISO connectors, sanitary connectors, quick disconnect connectors, or Luer Lock type connectors. In this manner, the entire concentrator system 10 may be operated without requiring that the housing 110 be opened during a concentration process until it is necessary or desired to remove the final concentrated volume of retentate within the retentate container 16 for testing and analysis.

In typical applications of the invention the harmful substances are preferably detected using culturable methods, molecular methods or immunoassay based methods. For culturable methods the harmful substance (i.e., microorganisms) in the retentate are preferably grown on growth media such as agar plates and allowed to incubate until colony forming units are visible. The resulting colony forming units are then preferably detected and counted, and the quantity of units is directly related to the amount of the harmful substance in the original sample. In these methods, retentate containing the harmful substance is preferably added directly to the growth media or a further concentration can occur through centrifugation or membrane filtration in which the centrifuged pellet or the membrane filter, respectively, is placed onto the growth media. If the harmful substance is a virus, a portion of the retentate containing the harmful substance is preferably placed onto a layer of viable cells growing on an agar plate. The harmful substance preferably has a cytopathic effect on the cells such that cell death occurs in the proximity of the virus. Cell death is visible on the layer of cells and the amount of the harmful substance is preferably correlated to the number of cell death areas on the plate.

For molecular methods, such as polymerase chain reaction, the harmful substance's DNA or RNA is preferably analyzed. The amount of molecular material is preferably used to estimate the amount of the harmful substance in the original sample of retentate.

For immunoassay based methods antibodies and/or antigens of the harmful substance are preferably added to portion of the retentate containing the harmful substance. The antibody/antigen reacts with the harmful substance, and the resulting product detected and quantified. The amount of the product is preferably directly related to the amount of the harmful substance in original sample.

Embodiments of sample concentrator systems of the present invention may provide various benefits and improvements over previously known concentrator systems. For example, embodiments of sample concentrator systems of the present invention may be automated, portable, easily configurable in the field, and may minimize or reduce the risk of exposure of an operator to potentially harmful pathogens or other harmful substances being concentrated by the concentrator systems.

Preferred embodiments, as described above, have been able to detect with 99% confidence 6 bacterial endospores in 100 liters of water. This sensitivity is required to be able to detect low-level harmful substances that would otherwise be undetectable. In preferred embodiments, the system is capable of detecting less than 100, even as low as 5 pathogens in 100 L of water container.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. A method for the detection of low-level harmful substances in a volume of fluid comprising:
   a) using a concentrator system to perform a method comprising:
      i) pumping at least 10 liters of fluid from a sample source through a filter and back into said sample source; said filter preventing the passage of at least one harmful substance;
      ii) diverting retentate from said filter into a container that is separate from said sample source;
      iii) recirculating at least part of said retentate in said container again through said filter;
      iv) circulating air to and from said container through an air filter;
      v) preventing the release of said retentate out of said concentrator system;
      vi) controlling the speed of a pump with a control system thereby maintaining a fluid pressure less than 25 PSI during said pumping of said fluid;
      vii) monitoring the quantity of retentate within said container with a control system and maintaining the quantity of retentate within a predetermined range comprising:
         (1) detecting a value of the volume or weight of said retentate;
         (2) controlling the amount of retentate diverted in said step of diverting retentate; and
         (3) selectively drawing in additional fluid from said sample source in order to maintain said quantity of retentate within said container within said predetermined range; and
   b) analyzing said retentate for the presence of at least one harmful substance.

2. The method for the detection of low-level harmful substances in a volume of fluid of claim 1 further comprising monitoring for leaks within said concentrator system.

3. The method for the detection of low-level harmful substances in a volume of fluid of claim 1:

a) further comprising transporting said container to a location different from said sample source; and
b) whereby said step of analyzing said retentate comprises analyzing said retentate at said different location.

4. The method for the detection of low-level harmful substances in a volume of fluid of claim 1 whereby said step of analyzing said retentate comprises analyzing said retentate with one or more analyzers within said concentrator system notifying a user of the results.

5. The method for the detection of low-level harmful substances in a volume of fluid of claim 1 whereby said filter comprises a blocking solution.

6. The method for the detection of low-level harmful substances in a volume of fluid of claim 1 whereby said filter comprises a blocking solution consisting essentially of water, polysorbate 80, an antifoaming agent, and sodium polyphosphate.

7. The method for the detection of low-level harmful substances in a volume of fluid of claim 1 further comprising after said step of pumping at least 10 liters of fluid from said sample source through said filter pumping an elution solution.

8. The method for the detection of low-level harmful substances in a volume of fluid of claim 1 further comprising after said step of pumping at least 10 liters of fluid from said sample source through said filter pumping an elution solution consisting essentially of water and 0.001% polysorbate 80.

9. The method for the detection of low-level harmful substances in a volume of fluid of claim 1 whereby said step of pumping at least 10 liters of fluid from said sample source through said filter comprises pumping fluid from said sample source using a single pump.

10. The method for the detection of low-level harmful substances in a volume of fluid of claim 1 whereby said step of pumping at least 10 liters of fluid from said sample source through said filter comprising pumping at least 100 liters of fluid.

11. The method for the detection of low-level harmful substances in a volume of fluid of claim 1 whereby said step of pumping at least 10 liters of fluid from said sample source through said filter comprising pumping 100 liters of fluid.

12. The method for the detection of low-level harmful substances in a volume of fluid of claim 1 whereby said step of pumping at least 10 liters of fluid from said sample source through said filter comprising pumping less than 2.9 liters per minute of fluid.

13. The method for the detection of low-level harmful substances in a volume of fluid of claim 1 whereby said step of controlling the amount of retentate diverted further comprises diverting less than 500 ml of retentate per 100 liters of fluid from said sample source into said retentate container.

14. The method for the detection of low-level harmful substances in a volume of fluid of claim 1 whereby said step of controlling the amount of retentate diverted further comprises diverting less than 250 ml of retentate per 100 liters of fluid from said sample source into said retentate container.

15. The method for the detection of low-level harmful substances in a volume of fluid of claim 1 whereby said step of analyzing said retentate comprises:
a) detecting an amount of one or more harmful substances in said retentate;
b) determining a concentration factor of said retentate from the ratio of a volume of said fluid that was pumped from said sample source to a volume of said monitored quantity of retentate; and
c) multiplying the amount of each harmful substance that has been detected in said retentate by said determined concentration factor thereby producing the amount of each harmful substance in said at least 10 liters of fluid that was pumped from said sample source.

16. The method for the detection of low-level harmful substances in a volume of fluid of claim 1 whereby said step diverting retentate from said filter into a container comprises directing said retentate along the inner walls of said container.

17. The method for the detection of low-level harmful substances in a volume of fluid of claim 1 whereby:
a) said step of detecting a value of the volume or weight of said retentate comprises a measuring device connected to said container; and
b) said step of diverting retentate from said filter comprises diverting retentate from said filter into said container in a manner that is perpendicular to said measuring device.

18. The method for the detection of low-level harmful substances in a volume of fluid of claim 1 whereby said step of circulating air to and from said container through an air filter comprises circulating air to and from said container through a High-efficiency Particulate Arrestance (HEPA) filter.

19. The method for the detection of low-level harmful substances in a volume of fluid of claim 1 whereby said filter comprises a plurality of hollow fibers extending through the body of said filter.

20. The method for the detection of low-level harmful substances in a volume of fluid of claim 19 whereby each of said hollow fibers of said filter comprises a longitudinally extending central lumen surrounded by a porous wall, said porous wall comprising a plurality of pores having an average pore size selected to prevent said at least one harmful substances from passing through said plurality of pores.

21. The method for the detection of low-level harmful substances in a volume of fluid of claim 20 whereby said porous walls of said hollow fibers of said filter have an average pore size of between about fifty nanometers (50 nm) and about two microns (2 μm).

22. The method for the detection of low-level harmful substances in a volume of fluid of claim 1 whereby said predetermined range is between a reduced volume level of retentate of 250 ml and a target volume of retentate of 750 ml.

23. The method for the detection of low-level harmful substances in a volume of fluid of claim 1 whereby said step of pumping at least 10 liters of fluid from said sample source through said filter and back into said sample source comprises pumping fluid through at least one loop of conduit and then through said filter.

24. The method for the detection of low-level harmful substances in a volume of fluid of claim 1 further comprising:
a) monitoring for leaks within said concentrator system;
b) after said step of pumping at least 10 liters of fluid from said sample source through said filter pumping an elution solution; and whereby
c) said filter comprises a blocking solution;
d) said step of pumping at least 10 liters of fluid from said sample source through said filter comprising pumping at least 100 liters of fluid;
e) said step of controlling the amount of retentate diverted further comprises diverting less than 500 ml of retentate per 100 liters of fluid from said sample source into said retentate container;
f) said step of diverting retentate from said filter into said container comprises directing said retentate along the inner walls of said container; and
g) said step of circulating air to and from said container through an air filter comprises venting air to and from said container through a High-efficiency Particulate Arrestance (HEPA) filter.

25. The method for the detection of low-level harmful substances in a volume of fluid of claim 24 further comprising:
- a) said step of pumping at least 10 liters of fluid from said sample source through said filter comprises pumping fluid from said sample source using a single pump;
- b) said step of pumping at least 10 liters of fluid from said sample source through said filter comprising pumping less than 2.9 liters per minute of fluid;
- c) said step of controlling the amount of retentate diverted further comprises diverting less than 250 ml of retentate per 100 liters of fluid from said sample source into said retentate container;
- d) said step of analyzing said retentate comprises:
  - i) detecting an amount of one or more harmful substances in said retentate;
  - ii) determining a concentration factor of said retentate from the ratio of a volume of said fluid that was pumped from said sample source to a volume of said monitored quantity of retentate; and
  - iii) multiplying the amount of each harmful substance that has been detected in said retentate by said determined concentration factor thereby producing the amount of each harmful substance in said at least 10 liters of fluid that was pumped from said sample source;
- e) said step of detecting a value at least relating to the volume or weight of said retentate comprises a measuring device connected to said container;

said step of diverting retentate from said filter comprises diverting retentate from said filter into said container in a manner that is perpendicular to said measuring device; and
- g) said step of pumping at least 10 liters of fluid from said sample source through said filter and back into said sample source comprises pumping fluid through at least one loop of conduit and then through a filter.

26. The method for the detection of low-level harmful substances in a volume of fluid of claim 25 whereby:
- a) said elution solution consisting essentially of water and polysorbate 80;
- b) said filter comprises said blocking solution that is consisting essentially of water, polysorbate 80, an antifoaming agent, and sodium polyphosphate;
- c) said step of pumping at least 10 liters of fluid from said sample source through said filter comprising pumping 100 liters of fluid;
- d) said reduced volume level of retentate is 250 ml;
- e) said target volume of retentate is 750 ml;
- f) said filter comprises a longitudinally extending central lumen surrounded by a porous wall, said porous wall comprising a plurality of pores having an average pore size selected to prevent said at least one harmful substances from passing through said plurality of pores; and
- g) said porous walls of said hollow fibers of said plurality of hollow fibers have an average pore size of between about fifty nanometers (50 nm) and about two microns (2 μm).

27. The method for the detection of low-level harmful substances in a volume of fluid of claim 26 further comprising:
- a) transporting said container to a location different from said sample source; and whereby
- b) said step of analyzing said retentate comprises analyzing said retentate at said different location.

28. The method for the detection of low-level harmful substances in a volume of fluid of claim 26 further comprising said step of analyzing said retentate comprises analyzing said retentate with one or more analyzers within said concentrator system notifying a user of the results.

* * * * *